United States Patent [19]
Pitt et al.

[11] Patent Number: 5,354,934
[45] Date of Patent: Oct. 11, 1994

[54] PULMONARY ADMINISTRATION OF ERYTHROPOIETIN

[75] Inventors: Colin G. Pitt, Thousand Oaks; Robert M. Platz, Half Moon Bay, both of Calif.

[73] Assignee: Amgen Inc., Thousand Oaks, Calif.

[21] Appl. No.: 13,514

[22] Filed: Feb. 4, 1993

[51] Int. Cl.$^5$ .......................... A61K 37/24; A61K 9/12
[52] U.S. Cl. .................................. 514/8; 424/85.1; 424/499
[58] Field of Search ................. 514/8, 2; 128/200.4; 435/69.1; 924/85.1; 424/499

[56] References Cited

U.S. PATENT DOCUMENTS

| | | | |
|---|---|---|---|
| 4,635,627 | 1/1987 | Gam | 128/200.14 |
| 4,703,008 | 10/1987 | Lin et al. | 435/240.2 |
| 5,011,678 | 4/1991 | Wang et al. | 424/45 |
| 5,013,718 | 5/1991 | Adamson et al. | 514/8 |

OTHER PUBLICATIONS

Patton, J. S., et al. (1992) *Adv. Drug Deliv. Rev.* 8: 179–96.
Hubbard, R. C., et al. (1989) *Proc. Natl. Acad. Sci. USA* 86: 680–84.
Peptide and Protein Drug Delivery, ed. V. Lee, Marcel Dekker, N.Y., 1990, pp. 1–11.
Adjei et al., Pharmaceutical Research, vol. 7, No. 6, pp. 565–569 (1990).
Hubbard et al., Annals of Internal Medicine, vol. 111, No. 3, pp. 206–212 (1989).
Smith et al., J. Clin. Invest., vol. 84, pp. 1145–1154 (1989).
Barrowcliffe et al., Thorax, vol. 4½, pp. 88–93.
Debs et al., The Journal of Immunology, vol. 140, pp. 3482–3488 (1988).
Newman et al., (1983) Thorax, vol. 38, pp. 881–886.
Braquet et al., (1989) J. Cardiovascular Pharmacology, vol. 13, supp. 5, pp. 143–146.

*Primary Examiner*—Robert J. Hill, Jr.
*Assistant Examiner*—David L. Fitzgerald
*Attorney, Agent, or Firm*—Daniel M. Chambers; Ron K. Levy; Steven M. Odre

[57] ABSTRACT

Erythropoietin (EPO) can be delivered systemically in therapeutically or prophylactically effective amounts by pulmonary administration using a variety of pulmonary delivery devices, including nebulizers, metered dose inhalers and powder inhalers. Aerosol administration of EPO in accordance with this invention results in significant elevation of red blood cell levels. EPO can be administered in this manner to medically treat or prevent anemia, as well as to treat or prevent other maladies related to erythropoiesis.

21 Claims, 4 Drawing Sheets

PULMONARY ADMINISTRATION OF ERYTHROPOIETIN

FIELD OF THE INVENTION

The present invention relates to the pulmonary administration of a therapeutic protein to a mammal and, more particularly, to the systemic administration of therapeutically effective amounts of erythropoietin (EPO) via the respiratory system.

BACKGROUND OF THE INVENTION

All mammals possess a hematopoietic (bloodforming) system that replenishes the multiplicity of blood cell types found in a healthy animal, including white blood cells (neutrophils, macrophages, and basophil/mast cells), clot forming cells (megakaryocytes, platelets), and red blood cells (erythrocytes). The average human male's hematopoietic system has been estimated to produce on the order of $4.5 \times 10^{11}$ granulocytes and erythrocytes every year, which is equivalent to an annual replacement of total body weight [Dexter et al., (1985) *BioEssays*, vol. 2: 154–158]. Current scientific understanding proposes that small amounts of specific hematopoietic growth factors direct the proliferation, differentiation, and maturation of each of the various hematopoietic cell types from a small population of pluripotent hematopoietic stem cells. These various growth factors act at different times on different cell populations, ultimately giving rise to a functional hematopoietic system.

One specific and vital role of the mammalian hematopoietic system is the production of erythrocytes, or red blood cells, which transport oxygen to the various tissues of the animal's body. The process of producing erythrocytes ("erythropoiesis") occurs continuously throughout an animal's life span to offset erythrocyte destruction. The typical red blood cell has a relatively short life-span, usually 100 to 120 days; *Gray's Anatomy*, Williams et al. eds., Churchill Livingstone, 1989, p. 665. Erythropoiesis is a precisely controlled physiological mechanism whereby sufficient numbers of erythrocytes are produced to enable proper tissue oxygenation, but not so many as to impede circulation.

Erythropoiesis is now known to be primarily controlled by the polypeptide erythropoietin (EPO), an acidic glycoprotein. Erythropoietin is produced as the result of the expression of a single copy gene located in a chromosome of a mammal. A DNA molecule encoding a DNA sequence for human EPO has been isolated and is described in U.S. Pat. No. 4,703,008, hereby incorporated by reference, and hereinafter referred to as the "Lin patent." Also, DNA molecules coding for EPO from monkeys [Lin et al., (1986) *Gene*, vol. 44, pp: 201–209] and mice [McDonald et al., (1986) *Mol. Cell Biol.*, pp: 842] have been described. The amino acid sequence for recombinant human EPO ("rHuEPO") is identical to the sequence for EPO obtained from human urinary sources. However, as could be expected, the glycosylation of rHuEPO differs from that of urinary EPO and human serum EPO. See, e.g. Starring et al. (1992), *J. Endocrin.*, vol. 134, pp: 459–484; Strickland et al. (1992), *J. Cell. Biochem.*, suppl. 16D, p. 324; Wide et al. (1990), *Br. J. Haematol.*, vol. 76, 121–127.

In a healthy mammal, EPO is present in the blood plasma in very low concentrations, as the tissues are being sufficiently oxygenated by the existing number of circulating erythrocytes. The EPO present stimulates the production of new erythrocytes to replace those lost to the aging process. Additionally, EPO production is stimulated under conditions of hypoxia, wherein the oxygen supply to the body's tissues is reduced below normal physiological levels despite adequate perfusion of the tissue by blood. Hypoxia may be caused by hemorrhaging, radiation-induced erythrocyte destruction, various anemias, high altitude, or long periods of unconsciousness. In contrast, should the number of red blood cells in circulation exceed what is needed for normal tissue oxygenation, EPO production is reduced.

However, certain disease states involve abnormal erythropoiesis. Until the advent of recombinant DNA technology, no EPO was available for therapeutic use. Today, the situation is different. Recombinant human EPO (rHuEPO) is being used therapeutically in a number of countries. In the United States, the U.S. Food and Drug Administration (FDA) has approved rHuEPO's use in treating anemia associated with end-stage renal disease. Patients undergoing hemodialysis to treat this disorder typically suffer severe anemia, caused by the rupture and premature death of erythrocytes as a result of the dialysis treatment. EPO is also useful in the treatment of other types of anemia. For instance, chemotherapy-induced anemia, anemia associated with myelodysplasia, those associated with various congenital disorders, AIDS-related anemia, and prematurity-associated anemia, may be treated with EPO. Additionally, EPO may play a role in other areas, such as helping to more quickly restore a normal hematocrit in bone marrow transplantation patients, in patients preparing for autologous blood transfusions, and in patients suffering from iron overload disorders. See e.g.U.S. Pat. No. 5,013,718, hereby incorporated by reference.

The effective use of EPO as a therapeutic agent requires that patients be administered small but highly precise doses of the protein in stable, pharmaceutically acceptable formulations. For an example of a current EPO formulation, see Sobata, J., *Erythropoietin in Clinical Applications*, Garnick, M., ed., Marcel Dekker, Inc., N.Y. (1990). Current therapy for end-stage renal disease calls for intravenous EPO administration within twelve hours of dialysis, three times a week. Alternatively, EPO may be administered to such patients by intravenous, intramuscular, intracutaneous, or subcutaneous injection.

The instant invention is based upon the unexpected discovery that EPO may be delivered in a therapeutically efficacious manner by direct administration of the protein to the lungs of a patient (hereinafter "pulmonary administration"). EPO delivered to the lung in this manner is absorbed into the patient's bloodstream for systemic distribution. This new route of EPO administration enables the rapid delivery of a specified medicament dosage to a patient without the necessity for injection. In addition, pulmonary administration more readily lends itself to self-administration by the patient.

There has been some prior success in the pulmonary administration of pharmaceutical compositions comprised of low molecular weight drugs, most notably in the area of beta-androgenic antagonists to treat asthma. Other low molecular weight, non-proteinaceous compounds, including corticosteroids and cromolyn sodium, have been administered systemically via pulmonary absorption. However, not all low molecular weight drugs can be efficaciously administered through the lung. For instance, pulmonary administration of aminoglycoside antibiotics, anti-viral drugs and anticancer drugs for systemic action has met with mixed success. In some cases, lack of delivery to the blood stream was attributed to the drug's inability to pass through the alveolar epithelium. In other cases, the drug was found to be irritating and bronchoconstrictive. Thus, even with low molecular weight substances, it is not at all predictable that the pulmonary delivery of such compounds will be an effective means of administration. See generally *Peptide and Protein Drug Delivery*, ed. V. Lee, Marcel Dekker, N.Y., 1990, pp. 1–11.

With respect to higher molecular weight pharmaceuticals, such as proteins, pulmonary delivery of such molecules is not unknown, although only a few examples have been quantitatively substantiated. Leuprolide acetate is a nonapeptide with luteinizing hormone releasing hormone (LHRH) agohist activity having low oral availability. Studies with animals indicate that inhalation of an aerosol formulation of leuprolide acetate results in meaningful levels in the blood. See Adjel et al., *Pharmaceutical Research*, Vol. 7, No. 6, pp. 565–569 (1990).

In contrast, Endothelin-1 (ET-1), a 21 amino acid vasoconstrictor peptide produced by endothelial cells, has been found to increase pulmonary inflation pressure but to have no significant effect on arterial blood pressure when administered by aerosol to guinea pigs. However, when administered intravenously, an important and sustained increase in arterial blood pressure was observed. See Braquet et al., *Journal of Cardiovascular Pharmacology*, Vol. 13, suppl. 5, s. 143–146 (1989).

The feasibility of delivering human plasma α1-antitrypsin to the pulmonary system using aerosol administration, with some of the drug gaining access to the systemic circulation, is reported by Hubbard et al., *Annals of Internal Medicine*, Vol. III, No. 3, pp. 206–212(1989).

Pulmonary administration of α-1-proteinase inhibitor to dogs and sheep has been found to result in passage of some of that substance into the bloodstream. See Smith et al., *J. Clin. Invest.*, vol. 84, pp. 1145–1154 (1989). Likewise, aerosolized α-1 anti-trypsin diffused across the lung epithelium and entered into systemic circulation in sheep and humans. See Hubbard et al., (1989) *Ann. Intern. Med., vol.* 111, pp. 206–212. However, vasoactive intestinal peptide, a small polypeptide with a molecular weight of 3,450 daltons (D) which causes bronchodilation when given intravenously in animals, including humans, lacks efficacy when administered by inhalation. See Barrowcliffe et al., *Thorax*, vol. 41/2, pp. 88–93 (1986).

Experiments with test animals have shown that recombinant human growth hormone, when delivered by aerosol, is rapidly absorbed from the lung and produces faster growth comparable to that seen with subcutaneous injection. See Oswein et al., "*Aerosolization of Proteins*", Proceedings of Symposium on Respiratory Drug Delivery II, Keystone, Colorado, March, 1990. Recombinant versions of the cytokines gamma interferon (IFN-γ) and tumor necrosis factor alpha (TNF-α) have also been observed in the bloodstream after aerosol administration to the lung. See Debs et al., The *Journal of Immunology*, Vol. 140, pp. 3482–3488 (1988). Likewise, Pitt et al. have recently demonstrated the feasibility of pulmonary delivery of granulocyte-colony stimulating factor (G-CSF) to mammals. See commonly-owned U.S. patent application Ser. No. 07/669,792, filed Mar. 15, 1991.

Despite these examples of protein delivery via the pulmonary route, it is not predictable whether a particular polypeptide can be delivered for systemic effect in such a manner. Various factors intrinsic to the polypeptide itself, the delivery device, and particularly the lung, or a combination of these factors, can influence the success of pulmonary administration.

With respect to the lung, its complexity presents several barriers to pulmonary administration. Initially, after passing through the nose or mouth, inhaled air (and any particles contained therein) moves into the respiratory tree, which is composed of numerous dichotomous branches between the trachea and the alveoli. Bronchi, bronchioles, and terminal bronchioles comprise the conducting zone. The epithelium of these conducting airways is pseudo stratified and largely ciliated. The more distal levels of branching form the transitional and respiratory zones, comprised of respiratory bronchioles, alveolar ducts, and alveoli, where gas exchange and pulmonary absorbtion occur. The respiratory zone, in contrast to the conducting zone, is non-ciliated and comprised of a single cell layer.

In the normal human male, it is estimated that the lungs contain $3 \times 10^8$ alveoli with a total surface area of approximately 140 $m^2$. Alveoli are thin walled pouches that represent as minimal a barrier to gaseous exchange between the atmosphere and blood as is possible without comprising the integrity of the lung. Correspondingly, capillary beds adjacent to the alveoli are estimated to share a surface area of 125 $m^2$ with the alveoli [*Gray's Anatomy, supra*]. Thus, each alveolus is in intimate association with numerous blood-bearing capillaries bringing oxygen-depleted blood from distal body tissues.

This air-blood barrier is comprised of the alveolar epithelium, the capillary endothelium, and the lymph-filled interstitial space separating these two cell layers. The mean thickness of the air-blood barrier in humans is 2.2 μm [Gehr et al. (1978), *Resp. Physiol.*, vol. 32, pp. 121–140], while the alveolar epithelium itself can be as thin as 0.05 μm. In the alveolar epithelium, adjacent cells overlap and are bound by non-leaky tight junctions, which, in conjunction with the non-leaky single cell layer comprising the capillary endothelium, limits the movement of fluids, cells, salts, proteins, and numerous other macromolecules from the blood and intercellular spaces into the lumen of the alveoli. Most molecules, including proteins and polypeptides, must be actively or passively transported across this barrier in the absence of lung injury.

In addition, within the lung certain epithelial cells secrete mucous to form a contiguous aqueous lining throughout the lung to promote the diffusion of oxygen into the blood. This layer of moisture, with its incumbent surface tension within the alveoli, requires that a surfactant be secreted to reduce this surface tension. Otherwise, the alveoli would collapse. In mammals, this surfactant, comprised mostly of lipid, appears to be made up of five layers [Stratton, C. J., *Cell Tissue Res.*, vol. 193, pp. 219–229 (1978)] and it can be a potential inhibitor of protein transport across the air-blood barrier.

Another protective system employed by the lung is the ciliary rejection current of the conducting zone. Here, numerous ciliated epithelial cells beat in a rhythmic one-way motion to propel the mucous lining overlaying the conducting airways towards the esophagus, where it is expelled from the respiratory system and moved into the digestive tract. Thus, particles impacting on these surfaces can be effectively removed prior to their penetration further into the lung.

Other cell types present in the alveolar lumen and in the interstitial space separating the alveolar epithelium from the capillary endothelium also serve as effective mechanisms for protecting the lung from and removing foreign material, such as protein-containing particles. Alveolar macrophages migrate from the blood across the air-blood barrier. These macrophages can phagocytose inhaled particles that reach the alveoli. These phagocytes may then migrate back into the lymphatic channels or to the base of the bronchial tree to be swept out of the lung by the ciliary rejection current. Additionally, other cell types, such as neutrophils and lymphocytes, can move into the alveoli from the blood to combat infection.

In view of the above, whether a particular therapeutic protein intended to have a systemic effect can be successfully delivered via the pulmonary route can not be predicted.

SUMMARY OF THE INVENTION

The present invention is based on the discovery that EPO can be administered systemically to a mammal via the pulmonary route and that such delivery results in comparable levels of therapeutic benefit as compared with current EPO administration methods. Pulmonary administration is accomplished by directing a stream of a therapeutically effective amount of EPO into the respiratory tract of the inhaling mammal. Importantly, and surprisingly, substantial amounts of EPO are thereby deposited in the lung and absorbed from the lung into the bloodstream, resulting in elevated levels of erythropoiesis. Moreover, this is accomplished without the necessity to resort to special measures such as the use of absorption enhancing agents or protein derivatives specifically designed to improve absorption. Pulmonary administration of EPO thus provides an effective non-invasive alternative to the systemic delivery of EPO by injection.

In light of the foregoing, it is the object of this invention to provide a method for the pulmonary administration of a therapeutically effective amount of EPO to a mammal, such as a human. In one aspect of the invention, the methods described herein involve directing a therapeutically effective amount of EPO into the patient's oral cavity during inhalation. Such delivery may be accomplished through the use of a mechanical device. Examples of mechanical devices useful in accordance with the methods of the invention include metered dose inhalers, powder inhalers, and nebulizers, particularly jet nebulizers and ultrasonic nebulizers.

EPO useful in the present invention may be obtained from natural sources, or more preferably it is derived from a eucaryotic host cell stably transformed with a DNA molecule coding for human EPO. In a particularly preferred embodiment, recombinant human EPO is derived from CHO cells stably transformed with DNA molecule encoding human EPO.

In a further aspect of the invention, the EPO delivered via the pulmonary route will be in a pharmaceutical composition comprising EPO and a pharmaceutically acceptable carrier. The composition may be embodied in an aqueous or non-aqueous solution, or particularly as a dry powder. When comprised of a dry powder, the particles should be small so as to allow their delivery to distal regions of the patient's lungs. Preferably, the particles should have a diameter of less than about 10 μm, while an especially preferred particle diameter range is from approximately 0.5 to 5 μm.

Yet another aspect of the claimed invention relates to the number of erythrocytes per μl of blood following pulmonary EPO administration. In one embodiment, pulmonary administration of a therapeutically effective amount of EPO leads to a red blood cell level in excess of about 1,000 erythrocytes per μl of blood. In a preferred embodiment of the invention, an erythrocyte level of about 5,000 to 6,000 red blood cells per μl of blood is attained. Included among the disorders that can be treated according to the instant methods are various anemias, including both chronic and acute anemias. Likewise, ailments characterized as iron overload disorders can also be effectively treated using the methods described herein.

Numerous aspects and advantages of the invention will be apparent to those skilled in the art upon consideration of the following detailed description which provides illumination of the practice of the invention in its preferred embodiments.

DETAILED DESCRIPTION

As used in this invention, the terms "EPO" and "erythropoietin" refer not only to rHuEPO as taught by the Lin patent and/or U.S. Pat. No. 4,667,016 (the Lai patent, hereby incorporated by reference) but also to biologically active analogs thereof. In general, EPO useful in the practice of this invention may be a native form isolated from mammalian organisms or, alternatively, a product of chemical synthetic procedures or eucaryotic host cell expression of exogenous DNA molecules encoding the erythropoietin amino acid sequences obtained by genomic or cDNA cloning or by gene synthesis. Suitable eucaryotic hosts include yeast (e.g., S. cerevisiae) and mammalian (e.g., Chinese hamster ovary (CHO), monkey) cells. Depending upon the host employed, the EPO expression product may be glycosylated with mammalian or other eucaryotic carbohydrates, or it may be non-glycosylated. The present invention contemplates the use of any and all such forms of EPO, although recombinant EPO, especially CHO-derived, is preferred for reasons of greatest commercial practicality.

EPO analogs useful in the practice of this invention include those having one or more amino acid additions, substitutions, and/or deletions as compared to either naturally-derived or rHuEPO. One particular embodiment of an analog comprising an additional amino acid is where an initial methionine amino acid residue is present at amino acid position -1. Substitution analogs may be particularly useful in that such analogs may enable greater and/or differential carbohydrate modifications as compared to either naturally-derived or rHuEPO.

Other useful EPO analogs include those having differential carbohydrate modifications, including EPO molecules containing different patterns of glycosylation, such as the addition or deletion of one or more oligosaccharide chains, differing levels of sialation, etc. See generally *Protein Glycosylation: Cellular, Biotechnical, and Analytical Aspects* (1991), edited by H.S. Conradt, VCH, N.Y, N.Y.

Additionally, other EPO analogs may also be generated. These include analogs wherein the protein is conjugated to another chemical substance, such as polyethylene glycol (PEG). For details, see U.S. Pat. No. 4,179,337, hereby incorporated by reference. Other useful chemical conjugations may include methylation, amidation, etc. Further, EPO (or a biologically active fragment thereof) conjugated to another protein molecule is also intended to fall within the scope of the term "erythropoietin" or "rHuEPO." For example, such conjugation may be accomplished by chemical or peptide linkers. See generally *Chemical Reagents for Protein Modification*, 2d. Ed. (1991) R. L. Lundblad, CRC, Boca Raton, Fla, pp. 287-304. As used herein, "EPO" also refers to chimeric protein molecules, wherein all or a portion of the primary amino acid sequence of erythropoietin is combined with a part or all of the primary amino acid sequence of one or more other polypeptide in a contiguous polypeptide chain. For a discussion on the generation of chimetic protein molecules, see *Chemical Reagents for Protein modification*, supra, hereby incorporated by reference. Proteins to which EPO may be linked, either by conjugation or by generation of a chimera, include G-CSF, GM-CSF, M-CSF, SCF, P-DGF, members of the interleukin family, and members of the FGF family.

Pulmonary delivery of pharmaceutical compositions intended for systemic administration to patients requires the deposition of a therapeutically active substance from a reservoir containing that active ingredient to an area of the patient's lungs capable transferring that substance, either actively or passively, to the patient's blood. The deposition is best accomplished by propelling a preparation comprised of an aqueous aerosol or solid particles containing the active ingredient into the lungs of the patient.

In the central airways of the lung, air flow is rapid and turbulent, but as the cross-sectional area of the more distal airways increases, the air flows in a smooth laminar manner [Fennet al., (1973) *Handbook of Physiology: Respiration*, Am. Physiol. Soc., Washington, D.C.]. Such smooth laminar flow enables microscopic particles containing EPO to be deposited in the alveoli of the patient receiving treatment.

Particle size is an important consideration in achieving particle deposition in the distal lung regions. Porush et al., reported that to reach the alveoli, small particles should be 0.5 $\mu$m to 7 $\mu$m in diameter [(1960) *Amer. Pharm. Assoc. Sci. Ed.*, vol. 49, p. 70]. Later, the preferred particle size for such deposition was reported to be less than 5 $\mu$m in diameter [Newman et al., (1983) *Thorax*, vol. 38, p. 881]. Along these lines, Utsumi et al. (PCT Patent Application No. WO 91/16038) disclosed the preparation of an aerosol composition comprised of solid, micronized human interferon or interleukin for pulmonary administration. In their preparation, the particles ranged from 0.5 $\mu$m to 10 $\mu$m in median diameter.

Devices capable of depositing aerosolized EPO formulations in the alveoli of a patient include nebulizers, metered dose inhalers, and powder inhalers. Other devices suitable for directing the pulmonary administration of EPO are also known in the art. All such devices require the use of formulations suitable for the dispensing of EPO in an aerosol. Such aerosols can be comprised of either solutions (both aqueous and non-aqueous) or solid particles. Nebulizers are useful in producing aerosols from solutions, while metered dose inhalers, dry powder inhalers, etc. are effective in generating small particle aerosols. Typically, each formulation is specific to the type of device employed and may involve the use of an appropriate propellant material, in addition to the usual diluents, adjuvants and/or carriers useful in EPO therapy. EPO formulations which can be utilized in the most common types of pulmonary dispensing devices to practice this invention are now described.

Nebulizer EPO Formulation

EPO formulations suitable for use with a nebulizer, either jet or ultrasonic, will typically comprise EPO dissolved in water at a concentration of, e.g., about 0.1 to 25 mg of EPO per mL of solution. The formulation may also include a buffer and a simple sugar (e.g., for protein stabilization and regulation of osmotic pressure), and/or human serum albumin ranging in concentration from 0.1 to 10 mg/ml. Examples of buffers which may be used are sodium acetate, citrate and glycine. Preferably, the buffer will have a composition and molarity suitable to adjust the solution to a pH in the range of 5 to 7. Generally, buffer molarities of from 2 mM to 50 mM are suitable for this purpose. Examples of sugars which can be utilized are lactose, maltose, mannitol, sorbitol, trehalose, and xylose, usually in amounts ranging from 1% to 10% by weight of the formulation.

The nebulizer formulation may also contain a surfactant to reduce or prevent surface induced aggregation of the protein caused by atomization of the solution in forming the aerosol. Various conventional surfactants can be employed, such as polyoxyethylene fatty acid esters and alcohols, and polyoxyethylene sorbitan fatty acid esters. Amounts will generally range between 0.001% and 4% by weight of the formulation. An especially preferred surfactant for purposes of this invention is polyoxyethylene sorbitan monooleate.

Two specific examples of commercially available nebulizers suitable for the practice of this invention are the Ultravent nebulizer, manufactured by Mallinckrodt, Inc., St. Louis, Mo., and the Acorn II nebulizer, manufactured by Marquest Medical Products, Englewood, Colo.

Metered Dose Inhaler EPO Formulation

EPO formulations for use with a metereddose inhaler device will generally comprise a finely divided powder. This powder may be produced by lyophilizing and then milling a liquid EPO formulation and may also contain a stabilizer such as human serum albumin (HSA). Typically, more than 0.5% (w/w) HSA is added. Additionally, one or more sugars or sugar alcohols may be added to the preparation if necessary. Examples include lactose maltose, mannitol, sorbitol, sorbitose, trehalose, xylitol, and xylose. The amount added to the formulation can range from about 0.01 to 200% (w/w), preferably from approximately 1 to 50%, of the EPO present. Such formulations are then lyophilized and milled to the desired particle size.

The properly sized particles are then suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant. This mixture is then loaded into the delivery device. An example of a commercially available metered dose inhaler suitable for use in the present invention is the Ventolin metered dose inhaler, manufactured by Glaxo Inc., Research Triangle Park, N.C.

Powder Inhaler EPO Formulation

Such EPO formulations will comprise a finely divided dry powder containing EPO and may also include a bulking agent, such as lactose, sorbitol, sucrose, or mannitol in amounts which facilitate dispersal of the powder from the device, e.g., 50% to 90% by weight of the formulation. The EPO should most advantageously be prepared in particulate form with an average particle size of less than about 10 μm (or micrometers), most preferably 1 to 5 μm, for most effective delivery to the distal lung.

An example of a powder inhaler suitable for use in accordance with the teachings herein is the Spinhaler powder inhaler, manufactured by Fisons Corp., Bedford, Mass.

The invention contemplates the administration of therapeutically effective amounts of erythropoietin via the pulmonary route. What constitutes a therapeutically effective amount of EPO will depend on the particular disease state or condition being treated. For instance, in the case of anemia, a therapeutically effective amount of EPO will be an amount sufficient to elevate the erythrocyte level in the blood. What constitutes a therapeutically effective amount in a particular case will depend on a variety of factors which the knowledgeable practitioner will take into account in arriving at the desired dosage regimen, including the normal red blood cell level for that subject, the severity of the condition or illness being treated, the degree of erythropoietic dysfunction, the physical condition of the subject, and so forth.

In general, a dosage regimen will be followed such that the normal erythrocyte level for the individual undergoing treatment is restored, at least in cases of abnormally low or depressed red blood cell counts. As used in this invention, anemia refers to a physical condition wherein the red blood cell count (or hematocrit) falls below the normal range for that particular species and that gender. "Hematocrit" is a measure of the erythrocyte content of a patient's blood as determined by low speed centrifugation of a blood sample, wherein the packed cell volume is compared to the total volume of the sample. Additional methods may also be used to determine the hematocrit, including automated blood cell counting. For humans, a normal red blood cell level is about $4.1-6.0\times10^6$ erythrocytes per microliter of blood in adult males and $3.9-5.5\times10^6$ red blood cells/μl in adult females. Correspondingly, hematocrit levels in humans also vary. In adult males, normal hematocrits range from 39.8 to 52.2%, the average being 46%. In contrast, the average human adult female hematocrit is 40.9%, and normally ranges from 34.9 to 46.9%. Clinical studies with patients having end stage renal disease, who suffer from chronic severe anemia (hematocrit below 30%) as a result of regular kidney dialysis, show that intravenously administered doses of 10-1500 μg rHuEPO/kg body weight thrice weekly are effective in elevating and/or maintaining erythrocyte levels in anemic patients. Eschbach, J., *Erythropoietin*, Erslev et al., eds., The Johns Hopkins University Press, 1991.

As those skilled in the art will recognize, the operating conditions for delivery of a suitable inhalation dose will vary according to the type of mechanical device employed. For some aerosol delivery systems, such as nebulizers, the frequency of administration and operating period will be dictated chiefly by the amount of EPO per unit volume in the aerosol. In general, higher concentrations of protein in the nebulizer solution and, correspondingly, the aerosol will require shorter operating periods. Some devices, such as metered dose inhalers, may produce higher aerosol concentrations than others and thus will be operated for shorter periods to give the desired result.

Other devices, such as powder inhalers, are designed to be used until a given charge of active material is exhausted from the device. The charge loaded into the device will be formulated accordingly to contain the proper inhalation dose amount of EPO for delivery in a single administration.

While EPO has been found useful in treating red blood cell-deficient conditions such as anemia associated with kidney dialysis, EPO is expected to also be effective in combating anemias associated with chemotherapy and other cytotoxic and/or cytostatic therapies where red blood cell levels are depressed below the norm. Additionally, EPO is useful in treating disorders, such as so-called iron overload disorders, characterized by excessive amounts of stored iron in the body (see U.S. Pat. No. 5,013,718). As further studies are conducted, information will emerge regarding appropriate dosage levels for the administration of EPO in these latter cases. It is expected that the present invention will be applicable as a non-invasive alternative in most instances where EPO is administered therapeutically by injection.

As mentioned, parenteral administration of EPO is known to cause an increase in the number of circulating erythrocytes in the blood. Studies were performed to demonstrate that inhalation of an aerosol of recombinant human EPO (rHuEPO) also causes an increase in the number of red blood cells. These inhalation studies were conducted by repeatedly exposing rats to an aerosol containing rHuEPO in a nose-only inhalation chamber. For comparison, rats were also administered EPO subcutaneously.

The rHuEPO employed was a CHO-derived recombinant expression product having the amino acid sequence shown in FIG. 6 of the aforementioned Lin patent comprising the entire rHuEPO polypeptide, from amino acid +1 through +166. The rHuEPO employed herein is produced according to the methods described in the Lin patent, supra. The rHuEPO produced according to the methods of Lin was then purified according to the methods described by Lai et al. in U.S. Pat. No. 4,667,016, hereby incorporated by reference. Following purification, the rHuEPO was prepared as an aqueous solution containing 2.34 mg rHuEPO per mL deionized water. This solution was then filtered through a Millex-GV (0.22 μm PVDF) filter and had a specific activity of 119,000 IU/mg.

EXAMPLE 1

Subcutaneous EPO Administration to Rats

To determine the hematocrit-increasing effect that rHuEPO has on rats, rHuEPO was administered subcutaneously at three dosage levels to male Sprague-Dawley rats (Simonsen Laboratories Inc., Gilroy, Calif.) weighing 130 to 200 g. rHuEPO was diluted in sterile phosphate-buffered saline (PBS), pH 7.4, containing 0.025% rat serum albumin to obtain the appropriate rHuEPO dose (500, 1,500, and 4,500 IU/kg) in a volume of 200 μL. One group of ten male rats was injected subcutaneously with a control solution of containing only 0.025% rat serum albumin in PBS, pH 7.4. Each of three rHuEPO dosages was injected subcutaneously into one of three groups of ten experimental animals. The animals were injected three times on alternating days for each dosage level. Following injection, the animals were returned to their cages and given free access to food and water. On the seventh day following the first rHuEPO administration, blood was drawn from each of the experimental animals by cardiac puncture and the hematocrit was measured.

Figure 1:
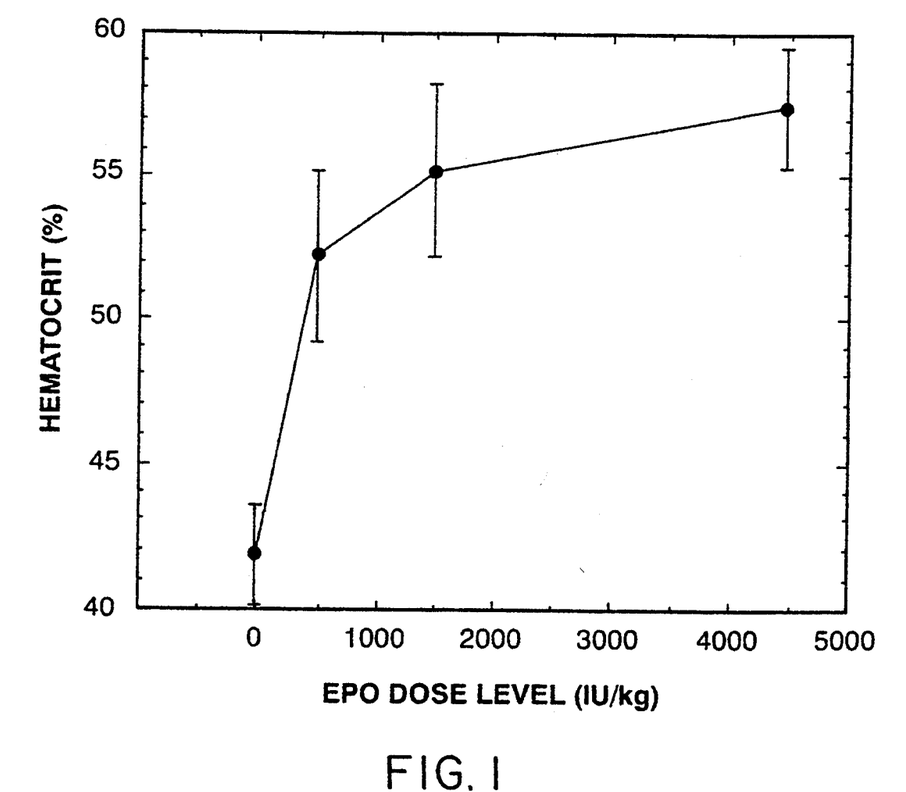
FIG. 1 graphically depicts the effect of subcutaneously administered rHuEPO on the hematocrit of normal rats. Three different dosages were tested: 500, 1,500, and 4,500 IU/kg. Results are expressed as the mean hematocrit (%) ± the standard deviation.
Figure 2:
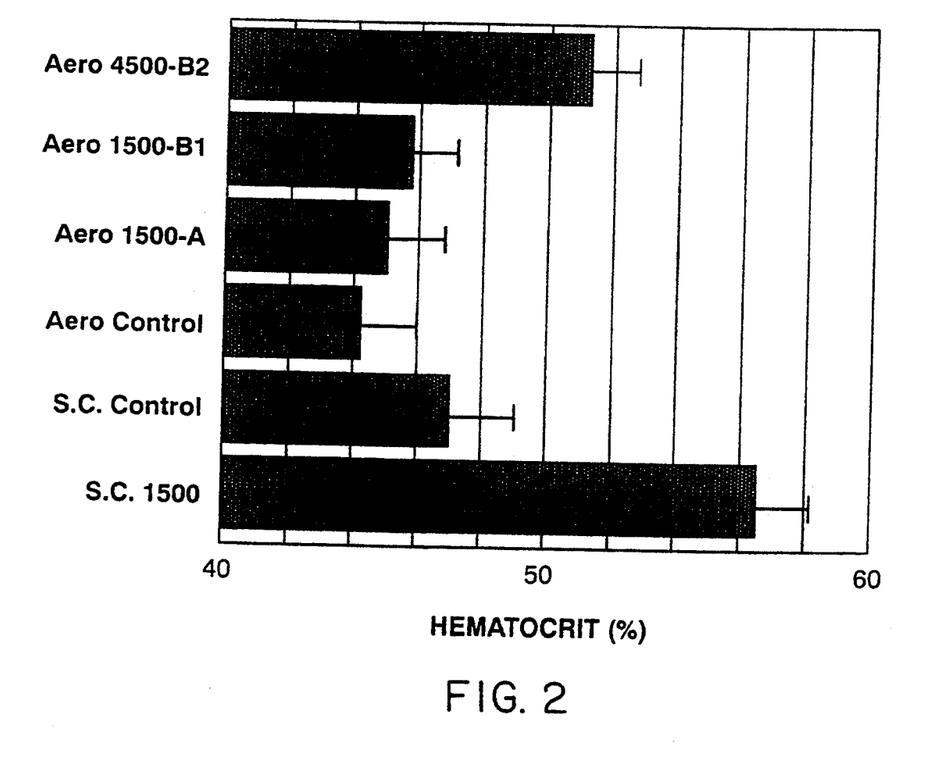
FIG. 2 is a bar graph showing the effect on the hematocrit of normal rats of rHuEPO administered in each of three different aerosol formulations (A, B1, and B2), as compared to the effect of subcutaneous administration. Results are expressed as the mean hematocrit (%) ± the standard deviation.

Rats that subcutaneously received 500 IU/kg of rHuEPO exhibited a 25% increase in hematocrit levels as compared to the placebo-treated controls (see FIG. 1). Those animals receiving higher dosages of rHuEPO showed significant, but non-linear, increases in hematocrit as compared to group that received 500 IU/kg per administration (see FIG. 1).

EXAMPLE 2

EPO Aerosol Characterization and Administration

After demonstrating that subcutaneous rHuEPO administration elicited an increased hematocrit in treated rats, efforts were undertaken to determine whether EPO could be delivered systemically via the pulmonary route. To conduct these experiments, an Acorn II jet nebulizer, supra, fitted with nose-only exposure chambers (In-Tox Products, Albuquerque, N.M.) was employed.

The EPO employed in the Acorn II was either of two formulations. Formulation A contained 0.67 mg/mL rHuEPO, 0.025% rat serum albumin, 15 mM phosphate buffer, pH 7.4, and 2% mannitol. Formulation B contained pure rHuEPO at a concentration of either 0.67 mg/mL (Formulation B1) or 2.34 mg/mL (Formulation B2), prepared by diluting concentrated rHuEPO with deionized water. It was estimated that a 0.67 mg/mL EPO solution would provide a 1,500 IU/kg dose to each rat over the course of a single aerosol exposure. Likewise, the 2.34 mg/mL formulation was designed to deliver a dose of 4,500 IU/kg over the course of an exposure. A control aerosol, consisting of the Formulation A constituents but no rHuEPO, was also prepared.

Aerosol exposure was accomplished by loading the Acorn II with 5 mL of one of the EPO formulations or the control solution. The compressed air-line pressure was adjusted to deliver an airflow of 10 L/min through the nebulizer. Groups of 20 rats were placed in tubular restrainers and loaded into the In-Tox exposure chamber. The aerosol was administered to the animals over a period of 10 minutes, by which time the EPO-containing solution had been completely dispensed from the nebulizer. After exposure, the experimental animals were returned to their cages and given free access to food and water.

Each aerosol formulation was delivered every other day for a total of three doses. On the seventh day after the first exposure, blood was drawn from each test animal by cardiac puncture and the blood analyzed for its hematocrit level.

During each exposure, particle size distribution was measured from one of the unused nose ports in the exposure chamber by attaching a QMC cascade impactor (California Measurements, Sierra Madre, Calif.). The mass median aerodynamic diameter (MMAD) and the geometric standard deviation (GSD) of the size distribution were calculated with the DISTFIT computer program (TSI, St. Paul, Minn.). Table 1 shows the results obtained for each formulation.

TABLE 1

| Formulation | Particle Size Distribution MMAD (μm) | GSD |
|---|---|---|
| Control | 1.10 ± 0.03 | 2.59 ± 0.28 |
| A | 1.14 ± 0.10 | 2.57 ± 0.13 |
| B1 | 0.74 ± 0.02 | 3.58 ± 0.04 |
| B2 | 0.85 ± 0.05 | 4.81 ± 0.19 |

Additionally, the aerosol concentration in the chamber was estimated by sampling 1 L/min through a 0.45 μm pore, polyvinylidene (PVDF), low protein binding filter (Millipore, Bedford, Mass.) attached to another unused chamber port. Aerosol concentration was estimated by measuring the weight gain of the filter and by analysis of the EPO collected thereon. EPO was extracted from the filter using 1.5 mL of a solution containing 5 mM CHAPS [see U.S. Pat. No. 4,372,888, hereby incorporated by reference; Hjelmeland, L. (1980) *Proc. Natl. Acad. Sci. USA*, vol. 77, p. 6368; Hjelmeland et al., (1983) *Anal. Blochem.*, vol. 130, p. 72] in 50 mM Tris buffer, pH 7.2, and 0.9% NaC1. The filter extract was analyzed by reverse-phase high-performance liquid chromatography (HPLC), radio-immuno assay (RIA), and by bioassay.

Reverse-phase HPLC analysis of the filter extract was conducted on a Hewlett Packard (Mountain View, Calif.) model 1050 HPLC with a 4.6 x 250 mm C4 bonded silica column (Vydac 214TP54) calibrated as follows: using standards of purified rHuEPO diluted in filtered deionized water containing 0.025% rat serum albumin and phosphate buffer, the column was run at a flow rate of 0.5 mL/min using a linear gradient of 0 to 55% acetonitrile (ACN) in 0.1% aqueous trifluoroacetic acid, wherein the ACN gradient increased 1% per minute. A dual channel UV detector recorded absorbances at 220 and 280 nm. At 280 nm, the HPLC response was linear over a range of 15 to 100 μg of rHuEPO. Under these conditions, rHuEPO eluted from the column at 52.3±1.5 min.

To analyze the filter extracts, 200 μL of each 1.5 mL extract described above was injected onto the column and analyzed as the standards had been. Table 2 depicts the total mass and EPO concentrations measured on the filters.

TABLE 2

| Formulation | Filter Extract Analysis | |
|---|---|---|
| | Powder Total Mass Concentration (μg/L) | EPO Concentration (μg/L) |
| Control | 437 ± 31.8 | 0.0 ± 0.0 |
| A | 457 ± 11.3 | 10.7 ± 2.5 |
| B1 | 10.0 ± 5.6 | 7.8 ± 0.8 |
| B2 | 40.7 ± 6.7 | 25.1 ± 2.7 |

Figure 3:
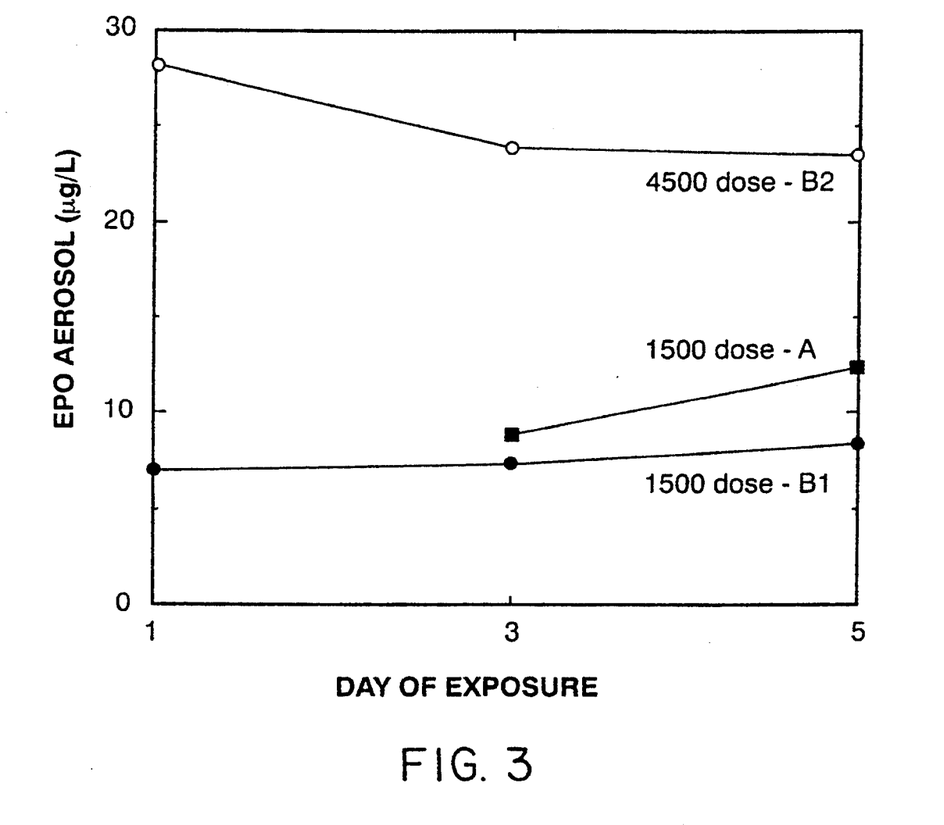
FIG. 3 presents the concentration of EPO measured in an aerosol generated for each of three formulations. Formulation A (1,500 IU/kg) is represented by (■-■), Formulation B1 (1,500 IU/kg) is represented by (●●), and (O-O) is represents Formulation B2 (4,500 IU/kg).

The EPO aerosol levels in the exposure chamber resulting from the various aerosol rHuEPO formulations are presented in FIG. 3. Seven days after the initial aerosol treatment, the average hematocrits (51.2±1.58%) of the 20 animals that received Formulation B2 were significantly higher (p>0.001) than the mean measured in the ten subcutaneous injection control animals (47.1±2.00%) and the aerosol control group (44.3±1.70%).

These data establish that EPO can be systemically delivered in therapeutically effective quantities. Also, the presence of mannitol had no apparent impact and the effectiveness of the EPO aerosol as compared to Formulation B1, which contained rHuEPO only.

Taken together, the results presented in Tables 1 and 2 and FIG. 3 show that the aerosol dosing was well controlled. The total mass concentration of the control aerosol was nearly equivalent to that obtained for Formulation A, which contained mannitol as a bulking agent (and which was also included in the control). Also, as expected, Formulation B2 produced an aerosolized EPO concentration of three times that for Formulation B1. The slightly higher aerosol concentration observed for Formulation A as compared to Formulation B1 is perhaps due to the presence of the bulking agent in the first formulation.

An estimate of the rHuEPO dose delivered by aerosol to a rat's lungs was made from the average concentration of EPO in the aerosol, the lung deposition fraction (0.29) [Dahlback et al., American Association of Aerosol Research, Reno, Nev., 1990], the resting ventilation rate for a rat (169 mL/min.), and the exposure period (10 min.). These estimated doses appear in Table 3 and correlate well with the targeted dosage levels.

TABLE 3

| EPO Exposure | Estimated EPO Aerosol Dosage Levels | | | | |
|---|---|---|---|---|---|
| | EPO Aerosol Concentration (μg/L) | EPO Dose (μg) | Average Weight (kg) | Normalized Dose (IU/kg) | Targeted Dose (IU/kg) |
| A | 10.7 ± 2.5 | 4.96 ± 1.16 | 0.227 | 2600 ± 608 | 1500 |
| B1 | 7.8 ± 0.8 | 3.67 ± 0.35 | 0.317 | 1359 ± 138 | 1500 |
| B2 | 25.1 ± 2.7 | 1.65 ± 1.25 | 0.314 | 4415 ± 473 | 4500 |

Figure 4:
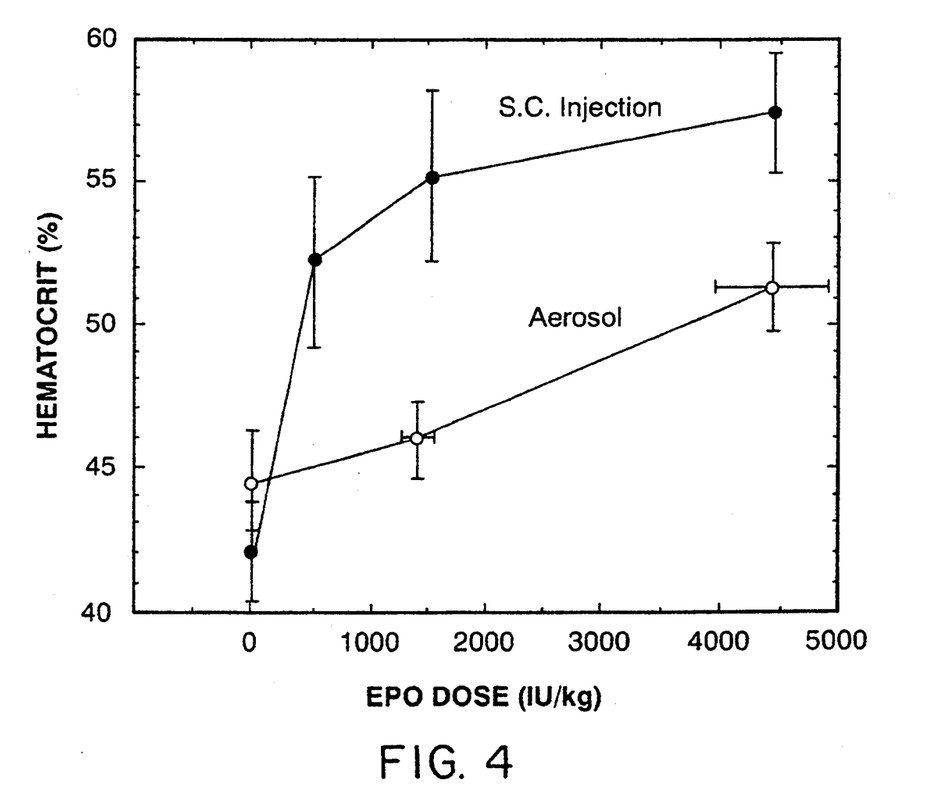
FIG. 4 graphically depicts the increase in hematocrit obtained by either pulmonary (O-O) or subcutaneous (●-●) administration.

FIG. 4 compares the hematocrits measured after exposure to the EPO aerosol formulations and to the hematocrits seen after subcutaneously dosing rats with various EPO concentrations. These results indicate that a 4,500 IU/kg dose of aerosolized EPO produced a hematocrit elevation equivalent to that obtained by a 500 IU/kg subcutaneous injection.

Radioimmunoassays (RIAs) were conducted on Formulation A, residual rHuEPO remaining in the nebulizer following aerosolization of Formulation A, and the amount of rHuEPO captured on a PVDF filter during the course of aerosol administration of Formulation A. The RIAs were conducted as follows: EPO samples (both experimental and standard samples) were incubated at 37° C. for two hours with rabbit anti-EPO antiserum in a total volume of 0.5 ml. Each sample was diluted to the final volume using a reaction diluent comprised of PBS, pH 7.4, containing 0.1% bovine serum albumin. After the two hour incubation, $^{125}$I-rHuEPO (Amersham Corp.) was added and the incubation continued at 4° C. overnight. Antibody-bound $^{125}$I-rHuEPO was separated from free $^{125}$I-rHuEPO by the addition of Tachisorb (goat antirabbit IgG conjugated to Staphylococcus aureus cells, Calbiochem, La Jolla, Calif., USA). The tubes were centrifuged to pellet the Tachisorb and the resulting pellets were washed in 10 mM Tris-HCl, pH 8.2, containing 150 mM NaCl, 2 mM EDTA, and 0.05% Triton X-100. Antibody-bound $^{125}$I-rHuEPO was then quantified by gamma counting.

In addition to RIAs, the in vivo biological activity of the rHuEPO in Formulation A delivered by nebulization was determined by using the exhypoxic polycythemic mouse bioassay (Cotes et al., Nature, vol. 191, pp. 1065-1067, 1961). This analysis enabled a determination as to whether rHuEPO retained its biological activity once aerosolized. The in vivo activity obtained from these assays was then converted to a mass concentration by dividing the results by 119,000 IU/μg EPO, the specific activity of the rHuEPO. Table 4 presents the results of the RIA and in vivo measurements.

TABLE 4

| EPO Activity Following Aerosolization | | | |
|---|---|---|---|
| Sample | Expected Conc. | EPO Conc. (RIA) | EPO Conc. (Bioasssay) |
| Formulation A | 0.67 mg/mL | 0.63 mg/mL | 0.64 mg/mL |
| Residual EPO in Nebulizer | 0.67 mg/mL | 0.75 mg/mL | 0.89 mg/mL |
| EPO from Filter Sample | 59.5 μg/mL$^a$ | 45.8 μg/mL | 64.0 μg/mL |

$^a$Measured by reverse-phase HPLC

Both the RIA and in vivo bioassay detected an increase in the EPO concentration in the solution remaining in the nebulizer after exposure, which is most likely due to water evaporation. See Mercer et al., Am. Ind. Hyg. Assoc. J., vol. 29, p. 66, 1968. Also, the close agreement between the RIA and bioassay results indicates that the specific activity of EPO was not adversely affected by the generation and drying of the aerosol.

While this invention has been specifically illustrated with regard to the use of aerosolized solutions and nebulizers, it is to be understood that any conventional means suitable for pulmonary delivery of a biological material may be employed to administer EPO in accordance with this invention. Indeed, there may be instances where a metered dose inhaler, or powder inhaler, or other device is preferable or best suits particular requirements. The foregoing description provides guidance as to the use of some of those devices. The application of still others is within the abilities of the skilled practitioner. Thus, this invention should not be viewed as being limited to practice by application of only the particular embodiments described.

What is claimed is:

1. A method comprising pulmonary administration to a mammal of a therapeutically effective amount of erythropoietin in the absence of an absoftion enhancing agent.

2. A method according to claim 1 comprising directing a stream of a therapeutically effective amount of erythropoietin into the oral cavity of the mammal while said mammal is inhaling.

3. A method according to claim 2 wherein the erythropoietin is administered as a pharmaceutical composition comprising EPO and a pharmaceutically compatible carrier.

4. A method according to claim 3 wherein the pharmaceutical composition is selected from the group consisting of an aqueous solution, a non-aqueous suspension, and a dry powder.

5. A method according to claim 4 wherein the pharmaceutical composition is a dry powder.

6. A method according to claim 5 wherein the dry powder comprises erythropoietin-containing particles, the particles having a diameter of less than 10 $\mu$m.

7. A method according to claim 5 wherein the erythropoietin-containing particles have a diameter ranging between 1 and 5 $\mu$m.

8. A method according to claim 2 wherein the erythropoietin is recombinant human erythropoietin.

9. A method according to claim 8 wherein the recombinant human erythropoietin is produced in a eucaryotic host cell stably transformed with a DNA molecule coding for human erythropoietin.

10. A method according to claim 9 wherein the host cell is a Chinese hamster ovary (CHO) cell.

11. A method according to claim 2 wherein a mechanical device directs a stream of a therapeutically effective amount of erythropoietin into the oral cavity of a mammal while the mammal is inhaling.

12. A method according to claim 11 wherein the mechanical device is selected from the group consisting of a nebulizer, a metered dose inhaler, and a powder inhaler.

13. A method according to claim 12 wherein the mechanical device is a nebulizer selected from the group consisting of a jet nebulizer and an ultrasonic nebulizer.

14. A method according to claim 13 wherein the device is a jet nebulizer.

15. A method according to claim 13 wherein the device is an ultrasonic nebulizer.

16. A method according to claim 2 wherein the mammal is a human.

17. A method according to claim 16 wherein the administration of a therapeutically effective amount of erythropoietin results in a red blood cell level in excess of 1000 erythrocytes per $\mu$L of blood.

18. A method according to claim 17 wherein the administration of a therapeutically effective amount of erythropoietin results in a red blood cell level of about 5000 to 6000 erythrocytes per $\mu$L of blood.

19. A method according to claim 1, wherein the method is employed for the treatment of anemia.

20. A method according to claim 1, wherein the method is employed for the prevention of anemia.

21. A method according to claim 1, wherein the method is employed for the treatment of and iron overload disorder.

* * * * *